US012611372B2

(12) United States Patent
Jung et al.

(10) Patent No.: US 12,611,372 B2
(45) Date of Patent: Apr. 28, 2026

(54) STRAIN AND USE THEREOF

(71) Applicant: LG HOUSEHOLD & HEALTH CARE LTD., Seoul (KR)

(72) Inventors: Haemin Jung, Seoul (KR); Mirim Kim, Seoul (KR); Fukushi Munemitsu, Sapporo (JP); Hojong Lee, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 83 days.

(21) Appl. No.: 18/546,052

(22) PCT Filed: Dec. 13, 2022

(86) PCT No.: PCT/KR2022/020240
§ 371 (c)(1),
(2) Date: Aug. 10, 2023

(87) PCT Pub. No.: WO2023/113431
PCT Pub. Date: Jun. 22, 2023

(65) Prior Publication Data
US 2024/0315951 A1 Sep. 26, 2024

(30) Foreign Application Priority Data

| | | |
|---|---|---|
| Dec. 14, 2021 | (KR) | 10-2021-0178893 |
| Dec. 14, 2021 | (KR) | 10-2021-0178894 |
| Dec. 14, 2021 | (KR) | 10-2021-0178895 |
| Dec. 14, 2021 | (KR) | 10-2021-0178896 |
| Dec. 14, 2021 | (KR) | 10-2021-0178897 |
| Nov. 29, 2022 | (KR) | 10-2022-0163002 |
| Dec. 7, 2022 | (KR) | 10-2022-0169776 |
| Dec. 7, 2022 | (KR) | 10-2022-0169777 |
| Dec. 7, 2022 | (KR) | 10-2022-0169778 |
| Dec. 9, 2022 | (KR) | 10-2022-0171985 |

(51) Int. Cl.

| | |
|---|---|
| *A61K 8/9728* | (2017.01) |
| *A61K 8/99* | (2017.01) |
| *A61Q 19/08* | (2006.01) |
| *C12N 1/185* | (2026.01) |
| *C12N 1/20* | (2006.01) |
| *C12R 1/11* | (2006.01) |
| *C12R 1/225* | (2006.01) |
| *C12R 1/865* | (2006.01) |

(52) U.S. Cl.
CPC ............. *A61K 8/9728* (2017.08); *A61K 8/99* (2013.01); *A61Q 19/08* (2013.01); *C12N 1/185* (2021.05); *C12N 1/20* (2013.01); *C12R 2001/11* (2021.05); *C12R 2001/225* (2021.05); *C12R 2001/865* (2021.05)

(58) Field of Classification Search
CPC .................................................... A61K 8/9728
See application file for complete search history.

(56) References Cited

U.S. PATENT DOCUMENTS

2012/0128755 A1 5/2012 Gruber et al.

FOREIGN PATENT DOCUMENTS

| | | | |
|---|---|---|---|
| CN | 109355228 A | 2/2019 | |
| CN | 110741073 A | 1/2020 | |
| JP | 2002-265326 A | 9/2002 | |
| JP | 2013-540124 A | 10/2013 | |
| JP | 2014-14355 A | 1/2014 | |
| KR | 10-2007-0090568 A | 8/2007 | |
| KR | 10-2012-0063025 A | 6/2012 | |
| KR | 101583600 B1 * | 1/2016 | .............. C12R 1/07 |
| KR | 10-1826145 B1 | 2/2018 | |
| KR | 10-2184119 B1 | 11/2020 | |
| WO | WO 2014/080666 A1 | 5/2014 | |
| WO | WO-2014140123 A1 * | 9/2014 | .......... A23L 29/065 |

OTHER PUBLICATIONS

Seo et al, Antioxidant and Skin-whitening Effects of Saccharomyces cerevisiae FT4-4 Isolated from Berries Grown in Sunchang. Journal of Life Science, Feb. 2021, vol. 31, No. 2, pp. 175-182 (Year: 2021).*
International Search Report for PCT/KR2022/020240 (PCT/ISA/210) mailed on Mar. 21, 2023.
Maibach et al., "Test concentrations and vehicles for dermatological testing of cosmetic ingredients", Contact Dermatitis, 1980, vol. 6, pp. 369-404.
Seo et al., "The Antioxidant and Skin-whitening Effects of Saccharomyces cerevisiae FT4-4 Isolated from Berries Grown in Sunchang", Journal of Life Science, Feb. 2021, vol. 31, No. 2, pp. 175-182.

* cited by examiner

Primary Examiner — Qiuwen Mi
(74) Attorney, Agent, or Firm — Birch, Stewart, Kolasch & Birch, LLP

(57) ABSTRACT

Methods are disclosed for preparing a fermentation product of a strain selected from the group consisting of *Saccharomyces cerevisiae* KCTC14779BP, *Saccharomyces cerevisiae* KCTC14780BP, *Lactobacillus fructivorans* KCTC14776BP, *Bacillus paramycoides* KCTC14777BP, and *Bacillus megaterium* KCTC14778BP. A cosmetic composition, a quasi-drug composition, or a food composition comprising any one or more of these strains, a culture of the strain, a fermented product of the strain, and a fraction of the culture or fermented product are also described, which may have excellent effects of improving skin and soothing sensitive skin.

9 Claims, No Drawings
Specification includes a Sequence Listing.

SEQUENCE LISTING

```
Sequence total quantity: 5
SEQ ID NO: 1          moltype = RNA  length = 818
FEATURE               Location/Qualifiers
source                1..818
                      mol_type = genomic RNA
                      organism = unidentified
SEQUENCE: 1
gcaattgggg ccatcctacc tgatttgagg tcaactttaa gaacattgtt cgcctagacg  60
ctctcttctt atcgataacg ttccaatacg ctcagtataa aaaaagatta gccgcagttg  120
gtaaaaccta aaacgaccgt acttgcatta tacctcaagc acgcaaagaa acctctcttt  180
ggaaaaaaaa catccaatga aaaggccagc aatttcaagt taactccaaa gagtatcact  240
cactaccaaa cagaatgttt gagaaggaaa tgacgctcaa acaggcatgc cccctggaat  300
accaaggggc gcaatgtgcg ttcaaagatt cgatgattca cggaattctg caattcacat  360
tacgtatcgc atttcgctgc gttcttcatc gatgcgagaa ccaagagatc cgttgttgaa  420
agttttaat  attttaaaat ttccagttac gaaaattctt gtttttgaca aaaatttaat  480
```

```
gaatagataa aattgtttgt gtttgttacc tctgggcccc gattgctcga atgcccaaag  540
aaaaagttgc aaagatatga aaactccaca gtgtgttgta ttgaaacggt tttaattgtc  600
ctataacaaa agcacagaaa tctctcaccg tttggaatag caagaaagaa acttacaagc  660
ctagcaagac cgcgcactta agcgcaggcc cggctggact ctccatctct tgtcttcttg  720
cccagtaaaa gctctcatgc tcttgccaaa acaaaaaaat ccattttcaa aattattaaa  780
tttctttaat gatccttccg cagtccccta accggaag                          818

SEQ ID NO: 2            moltype = RNA   length = 1658
FEATURE                 Location/Qualifiers
source                  1..1658
                        mol_type = genomic RNA
                        organism = unidentified
SEQUENCE: 2
atttatacag tgaaactgcg aatggctcat taaatcagtt atcgtttatt tgatagttcc  60
tttactacat ggtataactg tggtaattct agagctaata catgcttaaa atctcgaccc  120
tttggaagag atgtatttat tagataaaaa atcaatgtct tcggactctt tgatgattca  180
taataacttt tcgaatcgca tggccttgtg ctggcgatgg ttcattcaaa tttctgccct  240
atcaactttc gatggtagga tagtggccta ccatggtttc aacgggtaac ggggaataag  300
ggttcgattc cggagaggga gcctgagaaa cggctaccac atccaaggaa ggcagcaggc  360
gcgcaaatta cccaatccta attcaggag gtagtgacaa taaataacga tacagggccc   420
attcgggtct tgtaattgga atgagtacaa tgtaaatacc ttaacgagga acaattggag  480
ggcaagtctg gtgccagcag ccgcggtaat tccagctcca atagcgtata ttaaagttgt  540
tgcagttaaa aagctcgtag ttgaactttg ggcccggttg gccggtccga ttttttcgtg  600
tactggattt ccaacggggc cttccttct ggctaacctt gagtccttgt ggctcttggc    660
gaaccaggac ttttacttg aaaaaaattag agtgttcaaa gcaggcgtat tgctcgaata   720
tattagcatg gaataataga ataggacgtt tggttctatt ttgttggttt ctaggaccat  780
cgtaatgatt aataggggacg gtcggggggca tcagtattca attgtcagag gtgaaattcc  840
tggatttatt gaagactaac tactgcgaaa gcatttgcca aggacgtttt cattaatcaa  900
gaacgaaagt taggggatcg aagatgatca gataccgtcg tagtcttaac cataaactat  960
gccgactagg gatcgggtgg tgttttttta atgacccact cggcacctta cgagaaatca  1020
aagtctttgg gttctggggg gagtatggtc gcaaggctga aacttaaagg aattgacgga  1080
agggcaccac caggagtgga gcctgcggct taatttgact caacacgggg aaactcacca  1140
ggtccagaca caataaggat tgacagattg agagctcttt cttgattttg tgggtggtgg  1200
tgcatggccg ttcttagttg gtggagtgat ttgtctgctt aattgcgata acgaacgaga  1260
ccttaaccta ctaaatagtg gtgctagcat ttgctggtta tccacttctt agagggacta  1320
tcggtttcaa gccgatggaa gtttgaggca ataacaggtc tgtgatgccc ttagacgttc  1380
tgggccgcac gcgcgctaca ctgacggagc cagcgagtct aaccttggcc gagaggtctt  1440
ggtaatcttg tgaaactccg tcgtgctggg gatagagcat tgtaattatt gctcttcaac  1500
gaggaattcc tagtaagcgc aagtcatcag cttgcgttga ttacgtccct gccctttgta  1560
cacaccgccc gtcgctagta ccgattgaat ggcttagtga ggcctcagga tctgcttaga  1620
gaaggggggca actccatctc agagcggaga attggaca                         1658

SEQ ID NO: 3            moltype = RNA   length = 808
FEATURE                 Location/Qualifiers
source                  1..808
                        mol_type = genomic RNA
                        organism = unidentified
SEQUENCE: 3
gggtataaag cttttcgagc tcagcgtcag ttacagacta gacagccgcc ttcgccactg  60
gtgttcctcc atatatctac gcatttcacc gctacacatg gagttccact gtcctcttct  120
gcactcaagt ttcccagttt ccgatgcact tctccggtta agccgaaggc tttcacatca  180
gacttagaag accgcctgcg ctcgctttac gcccaataaa tccggacaac gcttgccacc  240
tacgtattac cgcggctgct ggcacgtagt tagccgtgac tttctggtta gataccgtcg  300
cgacgtgagc agttactctc acgcccgttc ttctctaaca acagagtttt acgagccgaa  360
accttcttc actcacgcgg cattgctcca tcagactttc gtccattgtg gaagattccc   420
tactgctgcc tcccgtagga gtctgggccg tgtctcagtc ccaatgtggc cgattaccct  480
ctcaggtcgg ctacgcatca ttgccttggt gagcctttat ctcaccaact agctaatgcg  540
ccgcggatcc atccaaaagc gatagcacaa aggccatctt tcaaacgaaa accatgtggt  600
tttcgttgtt atacggtatt agcatctgtt tccaggtgtt atccccttct tctgggcagg  660
ttatccacgt gttactcacc agttcgccac tcgctgctaa cttaagtcaa gttaatgcaa  720
gcatcaacta tcattaggcg cagctcgttc gacttgcatg tattaggcat gccgccagcg  780
ttcgtcctga gccatgtatc caaactct                                     808

SEQ ID NO: 4            moltype = RNA   length = 784
FEATURE                 Location/Qualifiers
source                  1..784
                        mol_type = genomic RNA
                        organism = unidentified
SEQUENCE: 4
ggccgtcagg ctttcgcgcc tcagtgtcag ttacagacca gaaagtcgcc ttcgccactg  60
gtgttcctcc atatctctac gcatttcacc gctacacatg gaattccact ttcctcttct  120
gcactcaagt ctcccagttt ccaatgaccc tccacggttg agccgtgggc tttcacatca  180
gacttaagaa accacctgcg cgcgctttac gcccaataat tccggataac gcttgccacc  240
tacgtattac cgcggctgct ggcacgtagt tagccgtgac tttctggtta ggtaccgtca  300
aggtgccagc ttattcaact agcacttgtt cttccctaac aacagagttt tacgacccga  360
aagccttcat cactcacgcg gcgttgctcc gtcagacttt cgtccattgc ggaagattcc  420
ctactgctgc ctcccgtagg agtctgggcc gtgtctcagt cccagtgtgg ccgatcaccc  480
tctcaggtcg gctacgcatc gttgccttgg tgagccgtta cctcaccaac tagctaatgc  540
gacgcgggtc catccataag tgacagccga agccgccttt caatttcgaa ccatgcggtt  600
```

-continued

```
caaaatgtta tccggtatta gccccggttt cccggagtta tcccagtctt atgggcaggt    660
tacccacgtg ttactcaccc gtccgccgct aacttcataa gagcaagctc ttaatccatt    720
cgctcgactt gcatgtatta ggcacgccgc cagcgttcat cctgagccat gttccaaaac    780
tcta                                                                 784

SEQ ID NO: 5           moltype = RNA  length = 783
FEATURE                Location/Qualifiers
source                 1..783
                       mol_type = genomic RNA
                       organism = unidentified
SEQUENCE: 5
tggggtcagc ctttcgcgcc tcagcgtcag ttacagacca aaaagccgcc ttcgccactg     60
gtgttcctcc acatctctac gcatttcacc gctacacgtg gaattccgct tttctcttct    120
gcactcaagt tccccagttt ccaatgaccc tccacggttg agccgtgggc tttcacatca    180
gacttaagaa accgcctgcg cgcgctttac gcccaataat tccggataac gcttgccacc    240
tacgtattac cgcggctgct ggcacgtagt tagccgtggc tttctggtta ggtaccgtca    300
aggtacaagc agttactctt gtacttgttc ttccctaaca acagagtttt acgacccgaa    360
agccttcatc actcacgcgg cgttgctccg tcagactttc gtccattgcg gaagattccc    420
tactgctgcc tcccgtagga gtctgggccg tgtctcagtc ccagtgtggc cgatcaccct    480
ctcaggtcgg ctatgcatcg ttgccttggt gagccgttac ctcaccaact agctaatgca    540
ccgcgggccc atctgtaagt gatagccgaa accatctttc aatcatctcc catgaaggag    600
aagatcctat ccggtattag cttcggtttc ccgaagttat cccagtctta caggcaggtt    660
gcccacgtgt tactcacccg tccgccgcta acgtcataga agcaagcttc taatcagttc    720
gctcgacttg catgtattag gcacgccgcc agcgttcatc ctgagccatg attcaaactc    780
taa                                                                 783
```

STRAIN AND USE THEREOF

REFERENCE TO ELECTRONIC SEQUENCE LISTING

The application contains a Sequence Listing which has been submitted electronically in XML format and is hereby incorporated by reference in its entirety. Said .XML copy, created on Jun. 20, 2023, is named "OPA22077.xml" and is 9,954 bytes in size. The sequence listing contained in this XML file is part of the specification and is hereby incorporated by reference herein in its entirety.

TECHNICAL FIELD

The present invention relates to a strain selected from the group consisting of *Saccharomyces cerevisiae* KCTC14779BP, *Saccharomyces cerevisiae* KCTC14780BP, *Lactobacillus fructivorans* KCTC14776BP, *Bacillus paramycoides* KCTC14777BP, and *Bacillus megaterium* KCTC14778BP; and a cosmetic composition, a quasi-drug composition, or a food composition comprising any one or more selected from the group consisting of the strain, a culture of the strain, a fermented product of the strain, and a fraction of the culture or fermented product.

BACKGROUND ART

Cosmetic ingredients are generally known to cause various skin problems such as inflammation, pimples, edema, etc. (Maibach, H. I., *Contact Dermatitis*, 6. 369-404, 1980). In addition, various substances used as raw materials for functional cosmetics also have a problem of low stability or insignificant effects on the skin.

In one example, retinoids, adenosine, animal placenta-derived proteins, *chlorella* extracts, etc. are known as cosmetics for improving skin wrinkles and elasticity. Retinol, which is the most widely known, has limitations in usage due to safety issues such as irritation when applied to the skin, and *chlorella* extracts, etc. have insignificant effects, and thus, it is difficult to substantially expect skin elasticity enhancement and wrinkle improvement effects.

Meanwhile, inflammation is a series of defensive responses which occurs to minimize the response and to restore the damaged area to its original state if a cell or tissue is damaged due to some causes, and it causes nerve and blood vessel, lymphatic vessel, humoral response, and cellular reactions, eventually resulting in pain, edema, redness, fever, etc., and thus leading to dysfunction. The causes of inflammation include physical factors such as trauma, frostbite, burns, radiation, etc., chemical factors such as acids, and immunological factors such as antibody reactions. In addition, inflammation is also caused by blood vessels or hormonal imbalances. Vasodilation is caused by various chemical mediators secreted by cells damaged by external stimuli, and as permeability increases, antibodies, complement, plasma, and phagocytic cells flock to the area of inflammation. This phenomenon causes erythema.

A drug that acts to remove an inflammatory source to eliminate inflammation and to reduce vital reaction and symptoms is called an anti-inflammatory agent. Until now, substances used for the purpose of anti-inflammation include non-steroids such as flufenamic acid, ibuprofen, benzydamine, indomethacin, etc., and steroids such as prednisolone, dexamethasone, etc., but the use thereof is limited because most of these substances have safety issues on the skin or stability issues when containing cosmetics.

Moisturizing cosmetic compositions generally used for the skin maintain a certain amount of moisture in human hair or skin so as to make them look soft and provide vitality, and function to prevent damage such as fissures, dryness, etc. That is, cosmetic compositions for skin moisturization are used for the purpose of beautifying the skin or hair and keeping them healthy by supplying over a certain amount of moisture to the skin or hair or maintaining the moisture.

Therefore, in recent years, extensive studies have been conducted on cosmetic compositions with excellent effects in terms of improving skin conditions (wrinkles, elasticity, etc.) or preventing skin aging or skin damage by providing excellent skin soothing, regeneration, moisturization, antioxidant, or anti-inflammatory effects.

DISCLOSURE

Technical Problem

The present inventors have conducted studies on raw materials that are safer and have excellent skin improvement effects from natural resources, and confirmed that the novel strain has a skin improvement effect and exhibits a significantly improved skin improvement effect compared to conventional yeast, *Lactobacillus*, and *Bacillus* fermented products, thereby completing the present invention.

Technical Solution

It is one object of the present invention to provide a strain selected from the group consisting of *Saccharomyces cerevisiae* deposited under Accession No. KCTC14779BP, under Accession *Saccharomyces cerevisiae* deposited No. KCTC14780BP, *Lactobacillus fructivorans* deposited under Accession No. KCTC14776BP, *Bacillus paramycoides* deposited under Accession No. KCTC14777BP, and *Bacillus megaterium* deposited under Accession No. KCTC14778BP.

It is another object of the present invention to provide a cosmetic composition for improving skin, including one or more among the strain, a culture of the strain, a fermented product of the strain, and a fraction of the culture or fermented product.

It is still another object of the present invention to provide a quasi-drug composition for improving skin, including any one or more among the strain, a culture of the strain, a fermented product of the strain, and a fraction of the culture or fermented product.

It is yet another object of the present invention to provide a food composition for improving skin, including any one or more among the strain, a culture of the strain, a fermented product of the strain, and a fraction of the culture or fermented product.

It is even another object of the present invention to provide a method for preparing a fermented product, including: fermenting with a strain selected from the group consisting of *Saccharomyces cerevisiae* deposited under Accession No. KCTC14779BP, *Saccharomyces cerevisiae* deposited under Accession No. KCTC14780BP, *Lactobacillus fructivorans* deposited under Accession No. KCTC14776BP, *Bacillus paramycoides* deposited under Accession No. KCTC14777BP, and *Bacillus megaterium* deposited under Accession No. KCTC14778BP.

It is further object of the present invention to provide a method for preparing a fraction, including: culturing a *Saccharomyces cerevisiae* strain deposited under Accession No. KCTC14780BP; and isolating the strain with water, a $C_1$ to $C_4$ alcohol, hexane, ethyl acetate, chloroform, or dichloromethane in the culture or fermented product of the strain.

Advantageous Effects

Since the *Saccharomyces cerevisiae, Lactobacillus fructivorans, Bacillus paramycoides*, or *Bacillus megaterium* strain, a culture of the strain, a fermented product of the strain, or a fraction of the culture or fermented product has excellent skin improvement effects, it can be widely used as cosmetic compositions, quasi-drug compositions, and food compositions for skin improvement. Accordingly, various industrial applications such as cosmetics, quasi-drugs, and foods can be expected.

DETAILED DESCRIPTION OF EMBODIMENTS

Hereinafter, the present invention will be described in detail. Meanwhile, each description and embodiment disclosed herein can be applied to other descriptions and embodiments with respect to common features. Additionally, all combinations of various elements disclosed herein fall within the scope of the present invention. Further, the scope of the present invention is not limited by the specific description described below.

One aspect of the present invention provides a strain selected from the group consisting of *Saccharomyces cerevisiae* deposited under Accession No. KCTC14779BP, *Saccharomyces cerevisiae* deposited under Accession No. KCTC14780BP, *Lactobacillus fructivorans* deposited under Accession No. KCTC14776BP, *Bacillus paramycoides* deposited under Accession No. KCTC14777BP, and *Bacillus megaterium* deposited under Accession No. KCTC14778BP.

As used herein, the term "*Saccharomyces cerevisiae*" refers to a species of yeast belonging to the genus *Saccharomyces* of the family Saccharomycesceae. This species has been instrumental in winemaking, baking, and brewing since ancient times and has been widely used.

The characteristics of *Saccharomyces cerevisiae* vary according to the growth area and natural environment conditions, and accordingly, the activity of strains and fermented products thereof may vary, and the *Saccharomyces cerevisiae* of the present invention may be derived from a fermented liquid, but is not limited thereto. Specifically, the *Saccharomyces cerevisiae* strain in the present invention may be a strain deposited under Accession No. KCTC14779BP or KCTC14780BP, but is not limited thereto.

As used herein, the term "*Lactobacillus fructivorans*" is a Gram-positive bacterium, and a species of *Lactobacillus* (probiotics) belonging to the genus Fructilactobacillus. It is found in wine, beer, grape must, diary, sauerkraut, meat and fish. The characteristics of *Lactobacillus fructivorans* vary according to the growth area and natural environment conditions, and accordingly, the activity of strains and fermented products thereof may vary, and the *Lactobacillus fructivorans* of the present invention may be derived from a fermented liquid, but is not limited thereto. Specifically, the *Lactobacillus fructivorans* strain in the present invention may be a strain deposited under Accession No. KCTC14776BP, but is not limited thereto.

As used herein, the term "*Bacillus paramycoides*" is a *Bacillus* species belonging to the phylum of firmicutes. The characteristics of *Bacillus paramycoides* vary according to the growth area and natural environment conditions, and accordingly, the activity of strains and fermented products thereof may vary, and the *Bacillus paramycoides* of the present invention may be derived from a fermented liquid, but is not limited thereto. Specifically, the *Bacillus paramycoides* strain in the present invention may be a strain deposited under Accession No. KCTC14777BP, but is not limited thereto.

As used herein, the term "*Bacillus megaterium, Bacillus subtilis*, or *Priestia megaterium*" is a rod-like, Gram-positive, mainly aerobic, spore forming bacterium found in widely diverse habitats. The term refers to a *bacillus* species belonging to the genus *Bacillus* and *Priestia*. It is widely used in feed additives for poultry, livestock, aquatic animals, ruminants, etc. The characteristics of *Bacillus megaterium* vary according to the growth area and natural environment conditions, and accordingly, the activity of strains and fermented products thereof may vary, and the *Bacillus megaterium* of the present invention may be derived from a fermented liquid, but is not limited thereto. Specifically, the *Bacillus megaterium* strain in the present invention may be a strain deposited under Accession No. KCTC14778BP, but is not limited thereto.

In the present invention, the fermented liquid may be prepared by fermentation for 6 months to 2 years, specifically for 9 months to 1 year and 6 months, more specifically for 1 year, and the fermented liquid may be a plant fermented liquid, but is not limited thereto.

In one embodiment of the present invention, fermented liquid was prepared, and it was confirmed that the *Saccharomyces cerevisiae, Lactobacillus fructivorans, Bacillus paramycoides* or *Bacillus megaterium* fermented products of the present invention exhibited excellent skin improvement effects compared to the fermented products of *Saccharomyces cerevisiae*, which is normal yeast, *Lactobacillus fructivorans*, which is normal *Lactobacillus*, or *Bacillus paramycoides* or *Bacillus megaterium*, which are normal *Bacillus*.

Another aspect of the present invention provides a cosmetic composition for improving skin, including one or more among the strain, a culture of the strain, a fermented product of the strain, and a fraction of the culture or fermented product.

As used herein, the term "strain" refers to a set of individuals derived from a single cell, which proliferates through asexual reproduction and has homogeneous genetic characteristics, and several strains (genetic variants) with different genetic characteristics may exist within one species. The strain in the present invention may mean *Saccharomyces cerevisiae, Lactobacillus fructivorans, Bacillus paramycoides* or *Bacillus megaterium*, and specifically a strain selected from the group consisting of *Saccharomyces cerevisiae* KCTC14779BP, *Saccharomyces cerevisiae* KCTC14780BP, *Lactobacillus fructivorans* KCTC14776BP, *Bacillus paramycoides* KCTC14777BP, and *Bacillus megaterium* KCTC14778BP, but is not limited thereto.

In the present invention, the strain may include cells, dried cells, lysates, etc. of the *Saccharomyces cerevisiae, Lactobacillus fructivorans, Bacillus paramycoides* or *Bacillus megaterium* strain. In particular, the dried cells may be spray-dried bacteria, freeze-dried bacteria, vacuum-dried bacteria, drum-dried bacteria, etc., and the lysates may be a product obtained by breaking the cell walls of the strain itself by chemical or physical force.

As used herein, the "culture" refers to a product obtained by culturing the strain in a medium. For example, the culture of the present invention may include components remaining in the medium after harvesting the strain in the culture medium of one or more strains selected from the group consisting of *Saccharomyces cerevisiae, Lactobacillus fructivorans, Bacillus paramycoides*, and *Bacillus megaterium*, or components of the culture medium containing the strain.

The culture may be the whole culture of the *Saccharomyces cerevisiae, Lactobacillus fructivorans, Bacillus paramycoides*, and/or *Bacillus megaterium* strain, supernatants, lysates, fractions thereof, etc. In particular, the supernatant may be obtained by centrifuging the culture of the strain, the lysate may be obtained by physical treatment or sonication of the strain, and the fraction may be obtained by conducting centrifugation, chromatography, etc. on the culture, supernatant, lysate, etc.

The medium and other culture conditions used for culturing the strain of the present invention may be any medium used for conventional cultivation of microorganisms belonging to the genus *Saccharomyces, Lactobacillus*, and/or *Bacillus* without any particular limitation. Specifically, the strain of the present invention may be cultured under aerobic or anaerobic conditions in a conventional medium containing an appropriate carbon source, nitrogen source, phosphorus source, inorganic compound, amino acid, and/or vitamin, while adjusting temperature, pH, etc.

In the present invention, the carbon source may include carbohydrates, such as glucose, fructose, sucrose, maltose, etc.; sugar alcohols, such as mannitol, sorbitol, etc.; organic acids, such as pyruvic acid, lactic acid, citric acid, etc.; amino acids, such as glutamate, methionine, lysine, etc., but is not limited thereto. Additionally, the carbon source may include natural organic nutrients such as starch hydrolysate, molasses, blackstrap molasses, rice bran, cassava, sugar cane molasses, and corn steep liquor, etc., and carbohydrates such as glucose and sterilized pretreated molasses (i.e., molasses converted to reducing sugar) may be used. In addition, various other carbon sources in an appropriate amount may be used without limitation. These carbon sources may be used alone or in a combination of two or more kinds.

The nitrogen source may include inorganic nitrogen sources, such as ammonia, ammonium sulfate, ammonium chloride, ammonium acetate, ammonium phosphate, ammonium carbonate, ammonium nitrate, etc.; and organic nitrogen sources, such as amino acids, peptone, NZ-amine, meat extract, yeast extract, malt extract, corn steep liquor, casein hydrolysate, fish or decomposition product thereof, defatted soybean cake or decomposition product thereof, etc. These nitrogen sources may be used alone or in a combination of two or more kinds, but are not limited thereto.

The phosphorus source may include monopotassium phosphate, dipotassium phosphate, or corresponding sodium-containing salts, etc. Examples of the inorganic compounds may include sodium chloride, calcium chloride, iron chloride, magnesium sulfate, iron sulfate, manganese sulfate, calcium carbonate, etc.

Additionally, amino acids, vitamins, and/or appropriate precursors, etc. may be included in the medium. Specifically, L-amino acids, etc. may be added to the culture medium of the strain. Specifically, glycine, glutamate, and/or cysteine may be added, and if necessary, L-amino acids such as lysine, etc. may be further added, but is not necessarily limited thereto.

The medium or precursors may be added to a culture in a batch or continuous manner, but is not limited thereto.

In the present invention, the pH of the culture may be adjusted by adding a compound such as ammonium hydroxide, potassium hydroxide, ammonia, phosphoric acid, sulfuric acid, etc. during cultivation of the strain in an appropriate manner. In addition, bubble formation may be prevented during cultivation using an antifoaming agent such as fatty acid polyglycol ester. Further, oxygen gas or a gas containing oxygen may be injected to the culture order to maintain aerobic conditions of the culture; or nitrogen gas, hydrogen gas, or carbon dioxide may be injected to maintain anaerobic or microaerobic conditions, without the injection of gas.

The temperature of the culture may be in the range of 25° C. to 40° C., more specifically in the range of 28° C. to 37° C., but is not limited thereto. The cultivation may be continued until the desired amount of a useful material is obtained, and may be specifically carried out for 1 to 200 hours, but is not limited thereto.

As used herein, the term "fermentation" means that microorganisms are not putrefactive during the process of decomposing organic matter using their own enzymes. Fermentation reaction and decay reaction proceed by similar processes, but when decomposition produces useful substances, it is called fermentation, and when odorous or harmful substances are produced, it is called decay.

In the present invention, the method for obtaining the fermented product from the strain is not particularly limited, and may be obtained by inoculating the strain into a medium, culturing the strain at 20° C. to 40° C. for 1 hour to 200 hours with shaking, and then isolating the cells via centrifugation, followed by sonication to disrupt the cells, or may be obtained according to a method commonly used in the art or similar fields.

In the present invention, as for the medium inoculated with the strain, the type of medium is not limited as long as the strain can undergo fermentation.

In the present invention, the fermented product obtained from the strain may include not only the fermented material itself, but also all kinds of materials including fermented products produced from the strain, such as a culture medium of the strain in which the strain and the culture coexist, a fermented product obtained by filtering the strain from the culture medium, a fermented product obtained by sterilizing the strain from the culture medium and filtering the same, an extract obtained by extracting the fermented product or a culture medium containing the same, a diluted solution obtained by diluting the fermented product or an extract thereof, a dried product obtained by drying the fermented product or an extract thereof, and a lysate obtained by collecting and lysing the cells of the strain, etc.

As used herein, the term "fraction" refers to a product obtained by performing fractionation to separate a specific component or a specific group from a mixture containing various elemental components.

The fractionation method for obtaining the fraction is not particularly limited, and may be carried out according to a method commonly used in the art. Non-limiting example of the fractionation method include a method of treating an extract obtained by extracting a culture or fermented product of a strain with a predetermined solvent, and thus obtaining a fraction from the extract.

The type of solvent used for obtaining the fraction is not particularly limited, and any solvent known in the art may be used. Non-limiting examples of the fraction solvent include polar solvents such as water, alcohol, etc.; and non-polar solvents such as hexane, ethyl acetate, chloroform, dichloromethane, etc. These may be used alone or in combination of two or more kinds. When the alcohol is used among the fraction solvents, a $C_1$ to $C_4$ alcohol may be preferably used.

In the present invention, the fraction may include a polypeptide extracted from the culture or fermented product of the strain.

As used herein, the peptide refers to a polymer in which amino acid units are artificially or naturally linked, is a substance in which two or more amino acids are linked, and is referred to as a tripeptide, an oligopeptide, or a polypeptide according to the number of amino acids. Specifically, in the present invention, the polypeptide may mean one containing 100 or more amino acids, but is not limited thereto.

In the present invention, the "polypeptide extracted from the culture or fermented product of the strain" refers to a peptide aggregate or polypeptide of a certain size or greater having functionality in the culture or fermented product, which is isolated after obtaining the culture or fermented product from the strain. In the present invention, the "polypeptide extracted from the culture or fermented product of the strain" is used interchangeably with the term "yeast polypeptide" or "fraction".

In the present invention, the method of isolating the fraction from the fermented product is not particularly limited, but the fraction may be obtained by filtering only the supernatant through concentration and precipitation (solvent, centrifugation process) from the lysate disrupted using the cells obtained by fermenting the strain, followed by spray drying.

As used herein, the term "skin improvement" may be any one or more selected from the group consisting of skin moisturization, wrinkle improvement, elasticity improvement, prevention of aging, skin soothing, skin regeneration, improvement of skin inflammation, skin whitening, antioxidation, anti-aging, skin protection from external stimuli, soothing of sensitive skin, improvement of sensitive skin, alleviation of erythema, alleviation of itchiness, enhancement of skin barrier function, and alleviation of skin irritation, but is not limited thereto.

As used herein, the term "improvement" refers to all activities that at least reduce the parameters associated with alleviation or treatment of conditions, e.g., the degree of symptoms, and may include any one or more among skin moisturization, wrinkle improvement, elasticity improvement, prevention of aging, skin soothing, skin regeneration, improvement of skin inflammation, skin whitening, antioxidation, anti-aging, skin protection from external stimuli, soothing of sensitive skin, improvement of sensitive skin, alleviation of erythema, alleviation of itchiness, enhancement of skin barrier function, alleviation of skin irritation, and alleviation of skin pain.

The skin improvement may be achieved through promoting hyaluronic acid synthesis, promoting collagen synthesis, increasing cell activity, inhibiting NO production, inhibiting melanin expression, scavenging free radicals, inhibiting prostaglandin E2 (PGE2) expression, increasing loricrin (LOR) expression, inhibiting TNF-a expression, or inhibiting TRPV1 activity, but is not limited thereto.

Specifically, the present inventors confirmed that the fermented product of Saccharomyces cerevisiae KCTC14779BP, the fermented product of Saccharomyces cerevisiae KCTC14780BP and/or yeast polypeptide, the fermented product of Lactobacillus fructivorans KCTC14776BP, the fermented product of Bacillus paramycoides KCTC14777BP, or the fermented product of Bacillus megaterium KCTC14778BP exhibited excellent skin improvement effects compared to the fermented products of normal yeast, normal Lactobacillus, normal Bacillus. More specifically, it was confirmed that the fermented product of Saccharomyces cerevisiae KCTC14779BP, the fermented product of Saccharomyces cerevisiae KCTC14780BP and/or yeast polypeptide, the fermented product of Lactobacillus fructivorans KCTC14776BP, the fermented product of Bacillus paramycoides KCTC14777BP, or the fermented product of Bacillus megaterium KCTC14778BP exhibited excellent effects of promoting collagen synthesis, promoting hyaluronic acid synthesis, increasing cell activity, inhibiting NO production, inhibiting melanin expression, scavenging free radicals, inhibiting prostaglandin E2 (PGE2) expression, increasing loricrin (LOR) expression, inhibiting TNF-a expression, or inhibiting TRPV1 activity, etc.

Therefore, it was confirmed that the Saccharomyces cerevisiae, Lactobacillus fructivorans, Bacillus paramycoides and/or Bacillus megaterium, fermented products thereof and/or fractions of the fermented products exhibited excellent skin improvement effects, such as wrinkle improvement, elasticity improvement, prevention of aging, skin moisturization, skin soothing, skin regeneration, improvement of skin inflammation, skin whitening, antioxidation, anti-aging, skin protection from external stimuli, soothing of sensitive skin, improvement of sensitive skin, alleviation of erythema, alleviation of itchiness, enhancement of skin barrier function, alleviation of skin irritation, and alleviation of skin pain, etc.

As used herein, the term "wrinkle" can be largely divided into facial wrinkles caused by facial expression muscles used to make facial expressions and fine wrinkles caused by overall or localized skin weakness. Specifically, wrinkles may be caused by genes, a decrease in collagen and elastic fibers present in the skin dermis, an external environment, etc. For the purpose of the present invention, wrinkles may be used in the sense of including all facial wrinkles or fine wrinkles, but is not limited thereto.

As used herein, the term "elasticity" is the force that tightly holds the skin when the skin is pressed with a finger. The term "elasticity improvement" or "elasticity enhancement" refers to increasing the elasticity of the skin by strengthening the structure of the subcutaneous fat layer of an individual, and may refer to increasing skin elasticity by the composition of the present invention.

As used herein, the term "aging" means a phenomenon in which body structures and functions deteriorate with the time, and the prevention of aging of the present invention is not limited to an extent as long as aging is improved, such as preventing, suppressing, delaying aging, etc. Wrinkle improvement and prevention of aging in the present invention may be caused by promoting collagen synthesis, but is not limited thereto.

As used herein, the term "collagen" is a fibrous protein largely found in most animals, especially mammals, covering almost all connective tissues in the body, such as skin and cartilage, and fibroblasts, the most common cells in the body, produce and secrete collagen. Gelatin, which is widely used in cooking or in the food and pharmaceutical industries, is the product obtained by irreversible hydrolysis of collagen. Since the decrease in collagen causes wrinkles and is the main cause of reducing skin elasticity, synthesis of collagen is essential for improving wrinkles and enhancing elasticity.

In one embodiment of the present invention, it was confirmed that the fermented product of Saccharomyces cerevisiae KCTC14779BP, the fermented product of Saccharomyces cerevisiae KCTC14780BP, which is a yeast, and/or yeast polypeptide, the fermented product of Lactobacillus fructivorans KCTC14776BP, which is a Lactobacillus, the fermented product of Bacillus paramycoides KCTC14777BP which is a Bacillus, exhibited superior collagen synthesis enhancement rate, and based on the results, it was confirmed that the yeast fermented product, yeast polypeptide, Lactobacillus fermented product or

9

*Bacillus* fermented product of the present invention had a remarkable effect on skin wrinkle improvement, elasticity enhancement, etc., (Tables 3, 4, 5, and 6).

As used herein, the term "skin moisturization" refers to all action that maintains the flexibility of the skin by supplying moisture to the skin or blocking evaporation of moisture and maintains a smooth surface by inducing uniform exfoliation of dead skin cells, and the term "dryness" refers to a state in which the skin is not sufficiently moisturized. The skin moisturization effect may help improve wrinkles and increase elasticity of the skin. Specifically, the skin moisturization may be caused by increasing hyaluronic acid production, but is not limited thereto.

As used herein, the term "hyaluronic acid" is a type of glycosaminoglycan and is a chain-shaped polymeric polysaccharide in which glucuronic acid and N-acetylglucosamine residues are repeatedly linked. Hyaluronic acid can contain water corresponding to 300 to 1000 times its own weight, and thus exhibits a moisturizing effect on the skin by binding with moisture.

In one embodiment of the present invention, it was confirmed that the fermented product of *Saccharomyces cerevisiae* KCTC14779BP, the fermented product of *Saccharomyces cerevisiae* KCTC14780BP, which is a yeast, and/or yeast polypeptide, the fermented product of *Lactobacillus fructivorans* KCTC14776BP, which is a *Lactobacillus*, the fermented product of *Bacillus paramycoides* KCTC14777BP, or the fermented product of *Bacillus megaterium* KCTC14778BP, which is a *Bacillus*, exhibited superior collagen synthesis enhancement rate, and based on the results, it was confirmed that the yeast fermented product, yeast polypeptide, or *Bacillus* fermented product of the present invention had a remarkable effect on prevention of aging, skin moisturization, etc., (Tables 7, 8, 9, 10, and 11).

As used herein, the term "regeneration" means inhibiting dysfunction of cells, tissue, or organs or restoring the function of cells, tissues, and organs. The dysfunction of cells, tissues, and organs may be caused by damage to cells, tissues, and organs. Such damage may be caused by various factors such as radiation therapy, drug therapy, surgery, infection, inflammation, degenerative disease, autoimmune disease, aging, etc. Meanwhile, the regeneration may be achieved by promoting cell differentiation, but is not limited thereto. In the present invention, "skin regeneration" may mean restoring back the damaged area of skin tissue. In the present invention, skin regeneration may be caused by enhancement of cell activity, but is not limited thereto.

In one embodiment of the present invention, while there was no effect on cell activity in the normal yeast fermented product, it was confirmed that the cell activity rate was significantly high in the fermented product of *Saccharomyces cerevisiae* KCTC14780BP, which is the yeast of the present invention, and/or the yeast polypeptide (Table 12).

As used herein, the term "skin soothing" refers to alleviating and relieving erythema, itchiness, or irritated skin or sensitive area, etc., and may include alleviation of skin irritation. For example, the skin soothing may include, but is not limited to, alleviation of skin itchiness, alleviation of skin pain, reduction of transdermal water loss and/or reduction of redness.

As used herein, the term "inflammation" is a kind of in vivo response to damage or infection of a specific tissue, and the main mediator is immune cells. The purpose of such inflammation is to suppress tissue damage as much as possible, remove infectious agents, and regenerate tissue. In the present invention, skin soothing and regeneration may be caused by inhibition of NO production, but is not limited thereto.

As used herein, the term "NO (nitric oxide)" plays various roles such as removing bacteria and tumors, regulating blood pressure, or mediating nerve transmission, etc. However, when an inflammatory reaction occurs, the expression of iNOS (inducible nitric oxide synthase) increases in related cells, resulting in the excess production of NO. Further, the excess production of NO causes tissue damage, genetic mutation, nerve damage, etc., and increases vascular permeability, thereby promoting inflammatory responses such as edema. While NO production is increased in inflamed cells, NO production is suppressed when the skin is soothed, and there exists an essential correlation therebetween.

In one embodiment of the present invention, it was confirmed that the fermented product of *Saccharomyces cerevisiae* KCTC14780BP, which is the yeast of the present invention, and/or yeast polypeptide, or the fermented product of *Lactobacillus fructivorans* KCTC14776BP, which is a *Lactobacillus*, also exhibited excellent NO production inhibitory ability as compared to the normal yeast or *Lactobacillus* fermented product, and based on the results, it was confirmed that the fermented product of *Saccharomyces cerevisiae* KCTC14780BP, which is the yeast of the present invention, and/or yeast polypeptide, or the fermented product of *Lactobacillus fructivorans* KCTC14776BP, which is a *Lactobacillus*, had skin soothing and inflammation improvement effects (Tables 13 and 14).

As used herein, the term "whitening" comprehensively includes a method of increasing the brightness of the skin whose brightness has decreased due to an excess of pigments such as melanin, or maintaining the brightness of the skin at a certain level, and the skin with increased brightness formed by the above method, etc., and may specifically mean skin whitening. The "skin whitening" may be understood as an improvement of symptoms, such as melasma and freckles, caused by an increase in melanin by inhibition of melanin production as tyrosinase activity is inhibited.

In one embodiment of the present invention, the excellent inhibition rate of melanin production was observed upon treatment with the fermented product of *Saccharomyces cerevisiae* KCTC14780BP, which is the yeast of the present invention, and/or yeast polypeptide, thereby confirming skin whitening effect (Table 15).

As used herein, the term "antioxidation" includes all action of inhibiting oxidation, and specifically mean an action of removing free radicals such as reactive oxygen species, but is not limited thereto. Reactive oxygen species can oxidize and destroy cells in the body, thereby exposing them to various diseases. In addition, since the skin has developed a complex antioxidant defense network to protect against reactive oxygen species, antioxidation can be associated with the effect of "protecting the skin from external stimuli".

As used herein, the term "anti-aging" means suppressing or alleviating the progress of aging. Aging of cells means oxidation of cells, and proper maintenance of reactive oxygen species may be addressed as a major principle in preventing oxidation of cells and aging of cells.

In one embodiment of the present invention, the free radical (reactive oxygen) scavenging effect was superior upon treatment with the fermented product of *Saccharomyces cerevisiae* KCTC14780BP, which is the yeast of the present invention, and/or yeast polypeptide, thereby confirming the effects of antioxidation, anti-aging and skin protection from external stimuli (Table 16).

As used herein the term "sensitive skin" refers to the skin that is more sensitive to reactions of external stimuli, allergic substances, environmental changes or internal causes of the human body, thereby easily causing irritation or dermatitis. It refers to complaints of various skin reactions such as erythema (redness), dead skin cells, blisters, etc., and subjective symptoms such as itching, stinging, irritation, pain, burning, etc., due to external stimuli such as cosmetics, etc., and internal causes of the body such as hormonal changes, etc.

In one embodiment of the present invention, the excellent effects of inhibiting the expression of erythema/itch-inducing factor (PGE2), increasing the expression of loricrin (LOR), a major component of the skin barrier, inhibiting the expression of inflammatory cytokine (TNF-a), and inhibiting the activity of skin nerve-stimulating inducer (TRPV1) were observed upon treatment with the fermented product of *Saccharomyces cerevisiae* KCTC14780BP, which is the yeast of the present invention, and/or yeast polypeptide, resulting in alleviation of erythema/itching, irritation/pain, which typical phenomena observed in sensitive skin, and strengthening the skin barrier, thereby confirming the effects of soothing and/or improving sensitive skin (Tables 17, 18, 19, and 20).

As used herein, the term "cosmetic composition" may be prepared in the form selected from the group consisting of solution, ointment for external use, cream, foam, nutritive cosmetic water, softening cosmetic water, perfume, facial mask, softening water, emulsion, makeup base, essence, soap, liquid washing agent, bath foam, sunscreen cream, sun oil, suspension, emulsion, paste, gel, lotion, powder, soap, surfactant-containing cleanser, oil, powder foundation, emulsion foundation, wax foundation, patch and spray, but is not limited thereto.

The cosmetic composition of the present invention may further include one or more cosmetically acceptable carrier mixed to general skin cosmetics. As common ingredients, for example, oil, water, surfactants, moisturizers, lower alcohols, thickening agents, chelating agents, colorings, preservatives, fragrances, etc. may be appropriately mixed, but are not limited thereto.

The cosmetically acceptable carrier included in the cosmetic composition of the present invention may vary depending on the formulation of the cosmetic composition.

When the cosmetic formulation of the present invention is an ointment, paste, cream or gel, animal oil, vegetable oil, wax, paraffin, starch, tragacanth, cellulose derivatives, polyethylene glycol, silicone, bentonite, silica, talc, zinc oxide, etc. may be used as a carrier ingredient, but the carrier ingredient is not limited thereto. These may be used alone or in a mixture of two or more thereof.

When the cosmetic formulation of the present invention is a solution or emulsion, solvents, solubilizing agents or emulsifying agents may be used as a carrier ingredient, and for example, water, ethanol, isopropanol, ethyl carbonate, ethyl acetate, benzyl alcohol, benzyl benzoate, propylene glycol, 1,3-butyl glycol oil, etc. may be used. In particular, cottonseed oil, peanut oil, maize germ oil, olive oil, castor oil and sesame seed oil, glycerol aliphatic ester, polyethylene glycol or aliphatic ester of sorbitan may be used, but the carrier ingredient is not limited thereto. These may be used alone or in a mixture of two or more thereof.

When the cosmetic formulation of the present invention is a suspension, liquid diluents such as water, ethanol or propylene glycol, suspending agents such as ethoxylated isostearyl alcohol, polyoxyethylene sorbitol ester and polyoxyethylene sorbitan ester, microcrystalline cellulose, aluminum metahydroxide, bentonite, agar, or tragacanth, etc. may be used as a carrier ingredient, but the carrier ingredient is not limited thereto. These may be used alone or in a mixture of two or more thereof.

When the cosmetic formulation of the present invention is a soap, alkali metal salts of fatty acids, salts of fatty acid hemiesters, fatty acid protein hydrolysates, isethionate, lanolin derivatives, aliphatic alcohol, vegetable oil, glycerol, sugars, etc. may be used as a carrier ingredient, but the carrier ingredient is not limited thereto. These may be used alone or in a mixture of two or more thereof.

When the cosmetic formulation of the present invention is a powder or spray, lactose, talc, silica, aluminum hydroxide, calcium silicate, polyamide powder, or a mixture thereof may be used as a carrier ingredient, and in particular, when it is a spray, a propellant such as chlorofluorohydrocarbon, propane/butane or dimethyl ether may be additionally included.

In one embodiment of the present invention, there may be provided a cosmetic composition for wrinkle improvement, elasticity improvement, prevention of aging or skin moisturization, including *Saccharomyces cerevisiae* KCTC14779BP, but is not limited thereto.

In one embodiment of the present invention, there may be provided a cosmetic composition for skin soothing, skin regeneration, improvement of skin inflammation, skin moisturization, wrinkle improvement, elasticity improvement, skin whitening, antioxidation, anti-aging, soothing of sensitive skin, improvement of sensitive skin, alleviation of erythema, alleviation of itchiness, or enhancement of skin barrier function, including *Saccharomyces cerevisiae* KCTC14780BP, but is not limited thereto.

In one embodiment of the present invention, there may be provided a cosmetic composition for wrinkle improvement, elasticity improvement, prevention of aging, skin soothing, improvement of skin inflammation, or skin moisturization, including *Lactobacillus fructivorans* KCTC14776BP, but is not limited thereto.

In one embodiment of the present invention, there may be provided a cosmetic composition for wrinkle improvement, elasticity improvement, prevention of aging or skin moisturization, including *Bacillus paramycoides* KCTC14777BP, but is not limited thereto.

In one embodiment of the present invention, there may be provided a cosmetic composition for skin moisturization, including *Bacillus megaterium* KCTC14778BP, but is not limited thereto.

Meanwhile, all components described in the present invention may be preferably included in the composition of the present invention within a range that does not exceed the maximum amount stipulated in the Regulations on the Safety Standards, etc. of Cosmetics and in the 'Safety and Technical Standards for Cosmetics' of China.

Still another aspect of the present invention provides a quasi-drug composition for improving skin, including any one or more among the strain, a culture of the strain, a fermented product of the strain, and a fraction of the culture or fermented product.

The "*Saccharomyces cerevisiae*", "*Lactobacillus fructivorans*", "*Bacillus paramycoides*", "*Bacillus megaterium*", "strain", "culture", "fermented product", "fraction", "yeast polypeptide", "skin improvement", "improvement", "wrinkle", "elasticity", "collagen", "aging", "skin moisturization", "hyaluronic acid", "regeneration", "skin soothing", "inflammation" and "NO", "whitening", "antioxidation", "skin protection from external stimuli", "anti-aging" and "sensitive skin" are as described above.

As used herein, the term "quasi-drug" may be one selected from the group consisting of body cleanser, sanitizer, detergent, kitchen cleanser, detergent for cleaning, toothpaste, mouthwash, wet wipe, cleanser, soap, hand soap, hair cleanser, hair softener, humidifying filler, mask, ointment or filter filler, but is not limited thereto.

The quasi-drug composition of the present invention may further include a pharmaceutically acceptable carrier, excipient, or diluent, if necessary, in addition to the above ingredients. The pharmaceutically acceptable carrier, excipient, or diluent is not limited as long as it does not impair the effect of the present invention and may include, for example, a filler, an extender, a binder, a wetting agent, a disintegrant, a surfactant, a lubricant, a sweetener, an aromatic, a preservative, etc.

Typical examples of the pharmaceutically acceptable carrier, excipient, and diluent of the present invention include lactose, dextrose, sucrose, sorbitol, mannitol, xylitol, maltitol, starch, gelatin, glycerin, acacia gum, alginate, calcium phosphate, calcium carbonate, calcium silicate, cellulose, methyl cellulose, microcrystalline cellulose, polyvinyl pyrrolidone, water, methyl hydroxybenzoate, propyl hydroxybeonzoate, talc, magnesium stearate, mineral oil, propylene glycol, polyethylene glycol, vegetable oil, injectable ester, witepsol, macrogol, tween 61, cacao butter, laurin butter, etc.

When a culture of the strain, a fermented product of the strain, and a fraction of the culture or fermented product is used as a quasi-drug, it may further contain one or more active ingredients exhibiting the same or similar functions. For example, it may contain ingredients capable of increasing skin beneficial bacteria, inhibiting skin harmful bacteria, skin soothing, improving skin inflammation, skin whitening, skin regeneration, and wound-healing known in the art. When additional ingredients capable of improving skin wrinkles, skin whitening, improving skin problems, or skin moisturization are included, the effects of wrinkle improvement, elasticity improvement, prevention of aging, skin soothing, skin regeneration and improvement of ski inflammation of the composition of the present invention may be further enhanced. When the above additional ingredients are added, skin safety, easiness of formulation, and stability of effective ingredients may be considered according to the combined use.

The quasi-drug composition may further include one or two or more ingredients selected from the group consisting of retinoic acid, TGF, an animal placenta-derived protein, betulinic acid, and a *chlorella* extract as a skin aging preventing or moisturizing ingredient known in the art; non-steroid such as flufenamic acid, ibuprofen, benzydamine, indomethacin, prednisolone, dexamethasone, allantoin, azulene, hydrocortisone as an anti-inflammatory ingredient known in the art; and derivatives thereof and various plant extracts. The additional ingredients may be contained in an amount of 0.0001% to 10% by weight based on the total weight of the composition, and the content range may be adjusted according to the requirements such as skin safety, easiness when formulating the strain of the present invention, a culture or fermented product of the strain, or a fraction extracted from the fermented product of the strain, etc.

The formulation methods, doses, usages, components, etc. of quasi-drugs may be appropriately selected from conventional techniques known in the art.

In one embodiment of the present invention, there may be provided a quasi-drug composition for wrinkle improvement, elasticity improvement, prevention of aging or skin moisturization, including *Saccharomyces cerevisiae* KCTC14779BP, but is not limited thereto.

In one embodiment of the present invention, there may be provided a quasi-drug composition for skin soothing, skin regeneration, improvement of skin inflammation, skin moisturization, wrinkle improvement, elasticity improvement, skin whitening, antioxidation, anti-aging, soothing of sensitive skin, improvement of sensitive skin, alleviation of erythema, alleviation of itchiness, or enhancement of skin barrier function, including *Saccharomyces cerevisiae* KCTC14780BP, but is not limited thereto.

In one embodiment of the present invention, there may be provided a quasi-drug composition for wrinkle improvement, elasticity improvement, prevention of aging, skin soothing, improvement of skin inflammation, or skin moisturization, including *Lactobacillus fructivorans* KCTC14776BP, but is not limited thereto.

In one embodiment of the present invention, there may be provided a quasi-drug composition for wrinkle improvement, elasticity improvement, prevention of aging or skin moisturization, including *Bacillus paramycoides* KCTC14777BP, but is not limited thereto.

In one embodiment of the present invention, there may be provided a quasi-drug composition for skin moisturization, including *Bacillus megaterium* KCTC14778BP, but is not limited thereto.

Yet another aspect of the present invention provides a food composition for improving skin, including any one or more among the strain, a culture of the strain, a fermented product of the strain, and a fraction of the culture or fermented product.

The "*Saccharomyces cerevisiae*", "*Lactobacillus fructivorans*", "*Bacillus paramycoides*", "*Bacillus megaterium*", "strain", "culture", "fermented product", "fraction", "yeast polypeptide", "skin improvement", "improvement", "wrinkle", "elasticity", "collagen", "aging", "skin moisturization", "hyaluronic acid", "regeneration", "skin soothing", "inflammation" and "NO", "whitening", "antioxidation", "skin protection from external stimuli", and "anti-aging" and "sensitive skin" are as described above.

As used herein, the term "food" may include all foods in a conventional sense, such as meats, sausages, breads, chocolates, candies, snacks, cookies, pizzas, ramens, other noodles, gums, dairy products including ice cream, various kinds of soups, beverages, teas, drinks, alcoholic beverages, vitamin complexes, health functional foods, etc., and is not limited as long as it can include one or more strains selected from the group consisting of *Saccharomyces cerevisiae* KCTC14779BP, *Saccharomyces cerevisiae* KCTC14780BP, *Lactobacillus fructivorans* KCTC14776BP, *Bacillus paramycoides* KCTC14777BP, and *Bacillus megaterium* KCTC14778BP, a culture of the strain, a fermented product of the strain, and a fraction of the culture or fermented product. Additionally, the food composition may be added to extracted juice, teas, jellies, juices, etc. which were prepared by the strain, a culture of the strain, a fermented product of the strain, and a fraction of the culture or fermented product according to the present invention as the main ingredient, and may be prepared in the form of pills, powders, granules, tablets, capsules, or liquids.

As used herein, the term "health functional food", which has the same meaning as the term "food for special health use (FoSHU)", refers to a food with high effects in medicinal and medical treatment, processed so as to efficiently exhibit a body modulating function as well as to provide nutrients. In particular, the term "functionality" refers to controlling nutrients for the structure or function of the human body or obtaining useful effects for hygienic purposes, such as physiological effects, etc. The food of the present invention may be prepared according to a method commonly employed in the art, and raw materials and ingredients commonly used in the art may be added when preparing the food. Additionally, the formulation of the food is not limited so long as it is recognized as a food. The food composition of the present invention may be prepared in various formulations, and the food composition of the present invention uses a food as a raw material unlike generic drugs, and thus has no side effects that may occur during long-term administration of the drugs, is highly portable, and may be administered as an adjuvant for enhancing the immune-boosting effects.

The health food refers to a food that has an active health maintenance or promotion effect compared to general food, and a health supplement food refers to a food intended for health supplement. In some cases, the terms functional food, health food, and health supplement food are used interchangeably.

Specifically, the health functional food is a food prepared by adding any one or more among one or more strains selected from the group consisting of *Saccharomyces cerevisiae* KCTC14779BP, *Saccharomyces cerevisiae* KCTC14780BP, *Lactobacillus fructivorans* KCTC14776BP, *Bacillus paramycoides* KCTC14777BP, and *Bacillus megaterium* KCTC14778BP, a culture of the strain, a fermented product of the strain, and a fraction of the culture or fermented product to food materials such as beverages, teas, spices, gum, and confectionery, etc., or a food prepared by means of encapsulation, powdering, or suspension. When the health functional food is ingested, a specific health effect may be obtained. However, unlike general drugs, since the health functional food uses food as a raw material, there is an advantage in that there are no side effects that may occur during long-term administration of the drugs.

The composition may further include a physiologically acceptable carrier, and the type of carrier is not particularly limited, and any carrier commonly used in the art may be used.

Additionally, the composition may contain additional ingredients that are conventionally used in food compositions so as to improve smell, taste, vision, etc. For example, the composition may contain vitamins A, C, D, E, B1, B2, B6, B12, niacin, biotin, folate, pantothenic acid, etc. In addition, the composition may contain minerals such as zinc (Zn), iron (Fe), calcium (Ca), chromium (Cr), magnesium (Mg), manganese (Mn), copper (Cu), and chromium (Cr), etc. Further, the composition may contain amino acids such as lysine, tryptophan, cysteine, valine, etc.

Additionally, the composition may also contain food additives, such as preservatives (potassium sorbate, sodium benzoate, salicylic acid, sodium dehydroacetate, etc.) disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclamate, saccharin, sodium, etc.), flavors (vanillin, lactones, etc.), swelling agents (alum, potassium D-hydrogen tartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

Any one or more among the *Saccharomyces cerevisiae* KCTC14779BP, *Saccharomyces cerevisiae* KCTC14780BP, *Lactobacillus fructivorans* KCTC14776BP, *Bacillus paramycoides* KCTC14777BP or *Bacillus megaterium* KCTC14778BP, a culture of the strain, a fermented product of the strain, and a fraction of the culture or fermented product may be added as it is or used in combination with other foods or food ingredients, and may be appropriately used according to a conventional method. The amount of mixed active ingredients may appropriately be determined depending on the purpose of use (prevention, health, or therapeutic treatment). In general, the food composition of the present invention may be added in an amount of 50 parts by weight or less, specifically 20 parts by weight or less, based on the food or beverage when preparing food or beverage. However, in the case of long-term administration for health and hygiene purposes, the active ingredients may be contained in an amount less than the above-described range, and because there is no problem in terms of safety, the active ingredients may be contained in an amount greater than the above-described range.

In one example, the food composition of the present invention may be used as a health beverage composition, and in such case, the food composition may further contain, as additional components, various flavoring agents or natural carbohydrates, as in conventional drinks. The aforementioned natural carbohydrates may include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. Natural sweetening agents such as thaumatin, a *stevia* extract, etc.; and synthetic sweetening agents such as saccharin, aspartame, etc. may be used as the sweetening agent. The ratio of the natural carbohydrates may be in a range of about 0.01 g to 0.04 g, specifically about 0.02 g to 0.03 g based on 100 mL of the composition of the present invention.

In addition to the aforementioned components, the health beverage composition may contain various nutritional supplements, vitamins, electrolytes, flavoring agents, coloring agents, pectic acid and salts thereof, alginic acid and salts thereof, organic acids, protective colloidal thickening agents, pH controlling agents, stabilizing agents, preservatives, glycerin, alcohols, or carbonating agents, etc. Moreover, the composition may contain pulp for preparing a natural fruit juice, a fruit juice drink or a vegetable drink. These ingredients may be used independently or in a mixture. The ratio of such additives is not important, but is generally chosen in a range of 0.01 to 0.1 parts by weight, based on 100 parts by weight of the composition of the present invention.

Specifically, any one or more among the *Saccharomyces cerevisiae* KCTC14779BP, *Saccharomyces cerevisiae* KCTC14780BP, *Lactobacillus fructivorans* KCTC14776BP, *Bacillus paramycoides* KCTC14777BP or *Bacillus megaterium* KCTC14778BP, a culture of the strain, a fermented product of the strain, and a fraction of the culture or fermented product may be contained in an amount of 00001% to 100% by weight based on the total weight of the food composition.

In one embodiment of the present invention, there may be provided a food composition for wrinkle improvement, elasticity improvement, prevention of aging or skin moisturization, including *Saccharomyces cerevisiae* KCTC14779BP, but is not limited thereto.

In one embodiment of the present invention, there may be provided a food composition for skin soothing, skin regeneration, improvement of skin inflammation, skin moisturization, wrinkle improvement, elasticity improvement, skin whitening, antioxidation, anti-aging, soothing of sensitive skin, improvement of sensitive skin, alleviation of erythema, alleviation of itchiness, or enhancement of skin barrier function, including *Saccharomyces cerevisiae* KCTC14780BP, but is not limited thereto.

In one embodiment of the present invention, there may be provided a food composition for wrinkle improvement, elasticity improvement, prevention of aging, skin soothing, improvement of skin inflammation, or skin moisturization, including *Lactobacillus fructivorans* KCTC14776BP, but is not limited thereto.

In one embodiment of the present invention, there may be provided a food composition for wrinkle improvement, elasticity improvement, prevention of aging or skin moisturization, including *Bacillus paramycoides* KCTC14777BP, but is not limited thereto.

In one embodiment of the present invention, there may be provided a food composition for skin moisturization, including *Bacillus megaterium* KCTC14778BP, but is not limited thereto.

Even another aspect of the present invention provides a method for preparing a fermented product, including: fermenting with a strain selected from the group consisting of *Saccharomyces cerevisiae* deposited under Accession No. KCTC14779BP, *Saccharomyces cerevisiae* deposited under Accession No. KCTC14780BP, *Lactobacillus fructivorans* deposited under Accession No. KCTC14776BP, *Bacillus paramycoides* deposited under Accession No. KCTC14777BP, and *Bacillus megaterium* deposited under Accession No. KCTC14778BP.

The "*Saccharomyces cerevisiae*", "*Lactobacillus fructivorans*", "*Bacillus paramycoides*", "*Bacillus megaterium*", "strain", and "fermented product" are as described above.

In the present invention, the fermented product may be obtained by inoculating *Saccharomyces cerevisiae* KCTC14779BP, *Saccharomyces cerevisiae* KCTC14780BP, *Lactobacillus fructivorans* KCTC14776BP, *Bacillus paramycoides* KCTC14777BP, or *Bacillus megaterium* KCTC14778BP into a medium, culturing the strains at 20° C. to 40° C. for 1 hour to 200 hours with shaking, and then isolating the cells via centrifugation, followed by sonication to disrupt the cells, but the method is not limited thereto. The medium used in the present invention may be the MRS medium, R2A medium, or LBS medium, but the type of medium is not limited as long as cultivation or fermentation of strains can be performed.

Further another aspect of the present invention provides a method for preparing a fraction, including: culturing a *Saccharomyces cerevisiae* strain deposited under Accession No. KCTC14780BP; and isolating the strain with water, a $C_1$ to $C_4$ alcohol, hexane, ethyl acetate, chloroform, or dichloromethane in the culture or fermented product of the strain.

The "*Saccharomyces cerevisiae*", "strain", and "fraction" are as described above.

Still further another aspect of the present invention provides the use of a cosmetic composition including any one or more among the strain of the present invention, a culture of the strain, a fermented product of the strain, and a fraction of the culture or fermented product for skin improvement.

Still further another aspect of the present invention provides the use of a quasi-drug composition including any one or more among the strain of the present invention, a culture of the strain, a fermented product of the strain, and a fraction of the culture or fermented product for skin improvement.

Still further another aspect of the present invention provides the use of a food composition including any one or more among the strain of the present invention, a culture of the strain, a fermented product of the strain, and a fraction of the culture or fermented product for skin improvement.

The "strain", "culture", "fermented product", "fraction", "yeast polypeptide", "skin improvement", and "improvement" are as described above.

Still further another aspect of the present invention provides a method for improving skin, including: applying or administering a composition including any one or more among the strain of the present invention, a culture of the strain, a fermented product of the strain, and a fraction of the culture or fermented product, as an active ingredient, to a subject.

The "strain", "culture", "fermented product", "fraction", "yeast polypeptide", "skin improvement", and "improvement" are as described above.

As used herein, the term "subject" may refer to all animals including humans, and the animal may include humans as well as mammals such as cows, horses, sheep, pigs, goats, camels, antelopes, dogs, cats, etc. in need of treating similar symptoms, but is not limited thereto.

As used herein, the term "application" means any method of contacting the composition of the present invention with the skin of a subject by any suitable method, and aims to absorb the composition into the skin through application. When the composition of the present invention is applied to the skin of a subject, it may have effects of wrinkle improvement, elasticity improvement, prevention of aging, skin moisturization, skin soothing, skin regeneration, improvement of skin inflammation, skin whitening, antioxidation, anti-aging, soothing of sensitive skin, improvement of sensitive skin, alleviation of erythema, alleviation of itchiness, and enhancement of skin barrier function, and it may include applying or administering the composition to a subject in an amount effective to exhibit the effect.

As used herein, the term "administration" collectively refers to providing a certain substance to a subject by any suitable method, and the administration route may be any conventional route so long as the substance can reach the targeted skin.

MODE FOR CARRYING OUT THE INVENTION

The present invention will be described in more detail by way of Examples. However, these Examples are provided for illustrative purposes only, and the scope of the invention is not intended to be limited by these Examples.

Example 1. Isolation of Yeast (*Saccharomyces cerevisiae* KCTC14779BP, KCTC14780BP), *Lactobacillus* (*Lactobacillus fructivorans* KCTC14776BP), *Bacillus* (*Bacillus paramycoides* KCTC14777BP, *Bacillus megaterium* KCTC14778BP) Strains The strains of *Saccharomyces cerevisiae* CF2-0w-17 and CF2-0w-22, which are novel yeasts, *Lactobacillus fructivorans* CF2-2w-20, which is a *Lactobacillus*, and *Bacillus paramycoides* CF1-0w-14 and *Bacillus megaterium* CF1-w2-30, which are *Bacillus*, were obtained from plant fermented liquid fermented for 1 year.

The *Saccharomyces cerevisiae* CF2-0w-17 and CF2-0w-22 strains were deposited at the Korean Collection for Type Cultures (KCTC) of the Korea Research Institute of Bioscience and Biotechnology under the Budapest Treaty on Nov. 16, 2021, with Accession Nos. KCTC14779BP and KCTC14780BP, respectively. It was confirmed that the strains have the 18s rRNA nucleotide sequences of SEQ ID NOs: 1 and 2, respectively.

The *Lactobacillus fructivorans* CF2-2w-20, *Bacillus paramycoides* CF1-0w-14, and *Bacillus megaterium* CF1-w2-30 strains were deposited at the Korean Collection for Type Cultures (KCTC) of the Korea Research Institute of Bioscience and Biotechnology under the Budapest Treaty on Nov. 16, 2021, with Accession Nos. KCTC14776BP, KCTC14777BP, and KCTC14778BP, respectively. It was confirmed that the strains have the 16s rRNA nucleotide sequences of SEQ ID NOs: 3, 4, and 5, respectively.

Example 2. Preparation of Yeast, *Lactobacillus* and *Bacillus* Fermented Products, and Polypeptides Extracted Therefrom

Example 2-1. Preparation of Yeast (*Saccharomyces cerevisiae* KCTC14779BP, KCTC14780BP) Fermented Products

*Saccharomyces cerevisiae* KCTC14779BP and KCTC14780BP strains were each inoculated into the medium and cultured with shaking, and then the cells of each strain were isolated by centrifugation. After suspending the cells in purified water, the cells were disrupted by sonication, and finally, *Saccharomyces cerevisiae* KCTC14779BP or KCTC14780BP fermented products were prepared. Specific conditions and compositions are shown in Table 1 below.

TABLE 1

| Strain | *Saccharomyces cerevisiae* KCTC14779BP, KCTC14780BP |
| --- | --- |
| Sonication | Amplitude 40, Process time 40 min, Pulse-ON time 1 s, Plus-OFF time 2 s |
| Concentration of yeast culture extract of *Saccharomyces cerevisiae* KCTC14779BP, KCTC14780BP | 5% |

Example 2-2. Preparation of Polypeptide Extracted from Yeast (*Saccharomyces cerevisiae* KCTC14780BP) Fermented Product and Fraction Containing the Same The *Saccharomyces cerevisiae* KCTC14780BP strain was inoculated into the medium and cultured with shaking. The cells were isolated by centrifugation, and then a lysate was obtained and concentrated. Thereafter, the resultant was suspended with alcohol in twice the amount of the lysate and centrifuged to isolate polypeptide fraction precipitated from the lysate, thus preparing a fraction containing the *Saccharomyces cerevisiae* KCTC14780BP polypeptide, the yeast of the present invention.

Example 2-3. Preparation of *Lactobacillus* (*Lactobacillus fructivorans* KCTC14776BP), *Bacillus* (*Bacillus* Paramycoides KCTC14777BP, *Bacillus megaterium* KCTC14778P) Fermented Products The *Lactobacillus fructivorans* KCTC14776BP, *Bacillus paramycoides* KCTC14777BP, and *Bacillus megaterium*

KCTC14778P strains were each inoculated into the medium and cultured with shaking, and then the cells of each strain were isolated by centrifugation. After suspending the cells in purified water, the cells were disrupted by sonication, and finally, *Lactobacillus fructivorans* KCTC14776BP, *Bacillus paramycoides* KCTC14777BP, and *Bacillus megaterium* KCTC14778P fermented products were prepared. Specific conditions and compositions are shown in Table 2 below.

TABLE 2

| Strain | *Lactobacillus fructivorans* KCTC14776BP, *Bacillus paramycoides* KCTC14777BP, *Bacillus megaterium* KCTC14778P |
| --- | --- |
| Sonication | Amplitude 40, Process time 40 min, Pulse-ON time 1 s, Plus-OFF time 2 s |
| Concentration of culture extract of *Lactobacillus fructivorans* KCTC14776BP, *Bacillus paramycoides* KCTC14777BP, *Bacillus megaterium* KCTC14778P | 5% |

Example 3. Confirmation of Collagen Synthesis Enhancement Effect of Yeast, *Lactobacillus* and *Bacillus* Fermented Products

Example 3-1. Confirmation of Collagen Synthesis Enhancement Effect of Yeast (*Saccharomyces cerevisiae* KCTC14779BP) Fermented Product Samples were treated with human dermal fibroblast for 48 hours at each concentration. The collagen synthesis rate was measured using a Procollagen Type I C-peptide (PIP) EIA kit. The collagen synthesis efficacy of the samples was calculated and measured as values in comparison with the negative control group (DMEM containing 0% serum).

In order to confirm the collagen synthesis enhancement effect of the *Saccharomyces cerevisiae* KCTC14779BP fermented product, the collagen synthesis rate was compared for normal cells, and normal cells treated with TGF-β, *Saccharomyces cerevisiae* KCTC14779BP fermented product, and normal yeast (*Saccharomyces cerevisiae* KCTC7296) fermented product (Table 3).

TABLE 3

| Sample | Collagen Synthesis Rate (% of control) |
| --- | --- |
| Normal cells (Negative control) | 0 |
| Normal cells + TGF-β (Positive control, 10 ppb) | 27.55 |
| *Saccharomyces cerevisiae* KCTC14779BP fermented product (1%) | 27.22 |
| Normal yeast fermented product (1%) | 9.81 |

As shown in the results of Table 3, it was confirmed that the collagen synthesis rate was increased when the normal cells were treated with the *Saccharomyces cerevisiae* KCTC14779BP fermented product. In particular, the increase rate of *Saccharomyces cerevisiae* KCTC14779BP fermented product was superior compared to that of the normal yeast fermented product prepared under the same conditions.

Example 3-2. Confirmation of Collagen Synthesis
Enhancement Effect of Yeast (*Saccharomyces
cerevisiae* KCTC14780BP) Fermented Product and
Fraction Containing Yeast Polypeptide The confirmation of collagen synthesis enhancement
effect was performed in the same manner as in Example 3-1,
and the collagen synthesis rate was compared for normal
cells, and normal cells treated with TGF-β, *Saccharomyces
cerevisiae* KCTC14780BP fermented product, and fraction
containing the yeast polypeptide (Table 4).

TABLE 4

| Sample | Collagen Synthesis Rate (% of control) |
|---|---|
| Normal cells (Negative control) | 0 |
| Normal cells + TGF-β (Positive control, 10 ng/mL) | 23.92 |
| Fraction containing normal yeast fermented product (1%) | 9.81 |
| *Saccharomyces cerevisiae* KCTC14780BP fermented product (1%) | 16.38 |
| Fraction containing *Saccharomyces cerevisiae* KCTC14780BP polypeptide (0.01%) | 16.99 |

As shown in the results of Table 4, it was confirmed that
the collagen synthesis rate was increased when the normal
cells were treated with the *Saccharomyces cerevisiae*
KCTC14780BP fermented product and the fraction contain-
ing the yeast polypeptide. In particular, the collagen syn-
thesis rates of *Saccharomyces cerevisiae* KCTC14780BP
fermented product and the fraction containing the yeast
polypeptide were superior compared to that of the normal
yeast fermented product prepared under the same condi-
tions.

Example 3-3. Confirmation of Collagen Synthesis
Enhancement Effect of *Lactobacillus* (*Lactobacillus
fructivorans* KCTC14776BP) Fermented Product The confirmation of collagen synthesis enhancement
effect was performed in the same manner as in Example 3-1,
and the collagen synthesis rate was compared for normal
cells, and normal cells treated with TGF-β, *Lactobacillus
fructivorans* KCTC14776BP fermented product, and normal
*Lactobacillus* (*Lactobacillus plantarum* KCTC3108) fer-
mented product (Table 5).

TABLE 5

| Sample | Collagen Synthesis Rate (% of control) |
|---|---|
| Normal cells (Negative control) | 0 |
| Normal cells + TGF-β (Positive control, 10 ppb) | 24.6 |
| *Lactobacillus fructivorans* KCTC14776BP fermented product (0.1%) | 21.77 |
| Normal *Lactobacillus* fermented product (0.1%) | 15.12 |

As shown in the results of Table 5, it was confirmed that
the collagen synthesis rate was increased when the normal
cells were treated with the *Lactobacillus fructivorans*
KCTC14776BP fermented product. In particular, the
increase rate of *Lactobacillus fructivorans* KCTC14776BP
fermented product was superior compared to that of the
normal *Lactobacillus* fermented product prepared under the
same conditions.

Example 3-4. Confirmation of Collagen Synthesis
Enhancement Effect of *Bacillus* (*Bacillus
paramycoides* KCTC14777BP) Fermented Product The confirmation of collagen synthesis enhancement
effect was performed in the same manner as in Example 3-1,
and the collagen synthesis rate was compared for normal
cells, and normal cells treated with TGF-β, *Bacillus paramy-
coides* KCTC14777BP fermented product, and normal
*Bacillus* (*Bacillus megaterium* KCTC3007) fermented prod-
uct (Table 6).

TABLE 6

| Sample | Collagen Synthesis Rate (% of control) |
|---|---|
| Normal cells (Negative control) | 0 |
| Normal cells + TGF-β (Positive control, 10 ppb) | 20.84 |
| *Bacillus paramycoides* KCTC14777BP fermented product (0.1%) | 33.41 |
| Normal *Bacillus* fermented product (0.1%) | 28.59 |

As shown in the results of Table 6, it was confirmed that
the collagen synthesis rate was increased when the normal
cells were treated with the *Bacillus paramycoides*
KCTC14777BP fermented product. In particular, the
increase rate of *Bacillus paramycoides* KCTC14777BP fer-
mented product was superior compared to that of the normal
*Bacillus* fermented product prepared under the same condi-
tions.

Accordingly, it was found that the *Saccharomyces cere-
visiae* KCTC14779BP fermented product, the *Saccharomy-
ces cerevisiae* KCTC14780BP fermented product and the
fraction containing the yeast polypeptide, the *Lactobacillus
fructivorans* KCTC14776BP fermented product and/or the
*Bacillus paramycoides* KCTC14777BP fermented product
of the present invention exhibited excellent effects in skin
wrinkle improvement, elasticity enhancement, etc.

Example 4. Confirmation of Hyaluronic Acid
Synthesis Enhancement Effect of Yeast,
*Lactobacillus* and *Bacillus* Fermented Products Example 4-1. Confirmation of Hyaluronic Acid
Synthesis Enhancement Effect of Yeast
(*Saccharomyces cerevisiae* KCTC14779BP)
Fermented Product Samples were treated with human keratinocyte HaCaT for
72 hours at each concentration. Hyaluronic acid synthesis
was compared with the control group (DMEM treatment
containing 0% serum) using Quantikine ELISA Hyaluronan
from R&D Systems to quantify the moisturizing ability
(Table 7).

TABLE 7

| Sample | Hyaluronic Acid Synthesis Rate (% of control) |
|---|---|
| Normal cells (Negative control) | 0 |
| Normal cells + Retinoic acid (Positive control, 1 ppm) | 13.6 |
| *Saccharomyces cerevisiae* KCTC14779BP fermented product (1%) | 12.5 |
| Normal yeast fermented product (1%) | 9.6 |

As shown in the results of Table 7, it was confirmed that the hyaluronic acid synthesis rate was increased when the normal cells were treated with the *Saccharomyces cerevisiae* KCTC14779BP fermented product. In particular, the increase rate of *Saccharomyces cerevisiae* KCTC14779BP fermented product was superior compared to that of the normal yeast fermented product prepared under the same conditions.

Example 4-2. Confirmation of Hyaluronic Acid Synthesis Enhancement Effect of Yeast (*Saccharomyces cerevisiae* KCTC14780BP) Fermented Product The confirmation of hyaluronic acid synthesis enhancement effect was performed in the same manner as in Example 4-1 (Table 8).

TABLE 8

| Sample | Hyaluronic Acid Synthesis Rate (% of control) |
|---|---|
| Normal cells (Negative control) | 0 |
| Normal cells + Retinoic acid (Positive control, 1 ppm) | 17.8 |
| Normal yeast fermented product (1%) | 12.6 |
| *Saccharomyces cerevisiae* KCTC14780BP fermented product (1%) | 93.8 |

As shown in the results of Table 8, it was confirmed that the hyaluronic acid synthesis rate was increased when the normal cells were treated with the *Saccharomyces cerevisiae* KCTC14780BP fermented product. In particular, the hyaluronic acid synthesis rate of *Saccharomyces cerevisiae* KCTC14780BP fermented product was superior compared to that of the normal yeast fermented product prepared under the same conditions.

Example 4-3. Confirmation of Hyaluronic Acid Synthesis Enhancement Effect of *Lactobacillus* (*Lactobacillus fructivorans* KCTC14776BP) Fermented Product The confirmation of hyaluronic acid synthesis enhancement effect was performed in the same manner as in Example 4-1 (Table 9).

TABLE 9

| Sample | Hyaluronic Acid Synthesis Rate (% of control) |
|---|---|
| Normal cells (Negative control) | 0 |
| Normal cells + Retinoic acid (Positive control, 1 ppm) | 27.6 |
| *Lactobacillus fructivorans* KCTC14776BP fermented product (0.1%) | 47.0 |
| *Lactobacillus fructivorans* KCTC14776BP fermented product (1%) | 86.6 |
| Normal *Lactobacillus* fermented product (0.1%) | 9.6 |
| Normal *Lactobacillus* fermented product (1%) | 39.2 |

As shown in the results of Table 9, it was confirmed that the hyaluronic acid synthesis rate was increased when the normal cells were treated with the *Lactobacillus fructivorans* KCTC14776BP fermented product. In particular, the increase rate of *Lactobacillus fructivorans* KCTC14776BP fermented product was superior compared to that of the normal *Lactobacillus* fermented product prepared under the same conditions.

Example 4-3. Confirmation of Hyaluronic Acid Synthesis Enhancement Effect of *Bacillus* (*Bacillus paramycoides* KCTC14777BP) Fermented Product The confirmation of hyaluronic acid synthesis enhancement effect was performed in the same manner as in Example 4-1 (Table 10).

TABLE 10

| Sample | Hyaluronic Acid Synthesis Rate (% of control) |
|---|---|
| Normal cells (Negative control) | 0 |
| Normal cells + Retinoic acid (Positive control, 1 ppm) | 22.0 |
| *Bacillus paramycoides* KCTC14777BP fermented product (1%) | 23.5 |
| Normal *Bacillus* fermented product (1%) | 17.1 |

As shown in the results of Table 10, it was confirmed that the hyaluronic acid synthesis rate was increased when the normal cells were treated with the *Bacillus paramycoides* KCTC14777BP fermented product. In particular, the increase rate of *Bacillus paramycoides* KCTC14777BP fermented product was superior compared to that of the normal *Bacillus* fermented product prepared under the same conditions.

Example 4-4. Confirmation of Hyaluronic Acid Synthesis Enhancement Effect of *Bacillus* (*Bacillus megaterium* KCTC14778BP) Fermented Product The confirmation of hyaluronic acid synthesis enhancement effect was performed in the same manner as in Example 4-1 (Table 11).

TABLE 11

| Sample | Hyaluronic Acid Synthesis Rate (% of control) |
|---|---|
| Normal cells (Negative control) | 0 |
| Normal cells + Retinoic acid (Positive control, 1 ppm) | 15.4 |
| *Bacillus megaterium* KCTC14778BP fermented product (1%) | 20.1 |
| Normal *Bacillus* fermented product (1%) | 17.1 |

As shown in the results of Table 11, it was confirmed that the hyaluronic acid synthesis rate was increased when the normal cells were treated with the *Bacillus megaterium* KCTC14780BP fermented product. In particular, the increase rate of *Bacillus paramycoides* KCTC14778BP fermented product was superior compared to that of the normal *Bacillus* fermented product prepared under the same conditions.

Accordingly, it was found that the *Saccharomyces cerevisiae* KCTC14779BP fermented product, the *Saccharomyces cerevisiae* KCTC14780BP fermented product, the *Lactobacillus fructivorans* KCTC14776BP fermented product, the *Bacillus paramycoides* KCTC14777BP fermented product and/or the *Bacillus megaterium* KCTC14778BP fermented product of the present invention exhibited excellent effects in skin wrinkle improvement, elasticity enhancement, moisturization, skin soothing, etc.

Example 5. Confirmation of Cell Activity Enhancement Effect of Yeast (*Saccharomyces cerevisiae* KCTC14780BP) Fermented Product and Fraction Containing Yeast Polypeptide Samples were treated with human dermal fibroblast for 48 hours at each concentration. The cell activity was measured using a CCK-8 kit. The cell activity efficacy of the samples was calculated and measured as values in comparison with the negative control group (DMEM containing 0% serum).

In order to confirm the cell activity enhancement effect of the *Saccharomyces cerevisiae* KCTC14780BP fermented product and the fraction containing the yeast polypeptide, the cell activity rate was compared for normal cells, and normal cells treated with FBS, *Saccharomyces cerevisiae* KCTC14780BP fermented product, normal yeast (*Saccharomyces cerevisiae* KCTC7296) fermented product, and fraction containing the yeast polypeptide (*Saccharomyces cerevisiae* KCTC14780BP) (Table 12).

TABLE 12

| Sample | Cell Activity Rate (% of control) |
| --- | --- |
| Normal cells (Negative control) | 0 |
| Normal cells + FBS (Positive control, 5%) | 17.55 |
| Normal yeast fermented product (1%) | No effect (−10.89) |
| *Saccharomyces cerevisiae* KCTC14780BP fermented product (1%) | 20.15 |
| Fraction containing *Saccharomyces cerevisiae* KCTC14780BP polypeptide (0.1%) | 60.76 |

As shown in the results of Table 12, it was confirmed that the cell activity rate was increased when the normal cells were treated with the *Saccharomyces cerevisiae* KCTC14780BP fermented product and the fraction containing the yeast (*Saccharomyces cerevisiae* KCTC14780BP) polypeptide. In particular, the increase rates of the *Saccharomyces cerevisiae* KCTC14780BP fermented product and the fraction containing the yeast polypeptide were superior compared to that of the normal yeast fermented product prepared under the same conditions.

Accordingly, it was found that the *Saccharomyces cerevisiae* KCTC14780BP fermented product and the fraction containing the yeast polypeptide of the present invention exhibited excellent effect in cell activity, etc.

Example 6. Confirmation of Skin Soothing and Inflammation Improvement Effects (Inhibition of NO Production) of Yeast and *Lactobacillus* Fermented Products

Example 6-1. Confirmation of Skin Soothing and Inflammation Improvement Effects (Inhibition of NO Production) of Yeast (*Saccharomyces cerevisiae* KCTC14780BP) Fermented Product and Fraction Containing Yeast Polypeptide Raw 264.7 cells were diluted for each concentration, treated with 1 µg/mL of LPS, and cultured for 24 hours. The NO production inhibitory ability was evaluated as follows using a NO assay kit (Table 13).

$$NO \text{ production inhibition ability } (\%) =$$

$$(1 - (NO \text{ production amount when sample is added}/$$

$$NO \text{ production amount when sample is not added}) \times 100$$

TABLE 13

| Sample | NO production inhibitory ability (% of control) |
| --- | --- |
| Normal cells (Negative control) | 0 |
| Normal cells + L-NMMA (Positive control, 20 µg/mL) | 47.9 |
| Normal yeast fermented product (0.01%) | 18.4 |
| *Saccharomyces cerevisiae* KCTC14780BP Fermented Product (0.01%) | 37.8 |
| Fraction containing *Saccharomyces cerevisiae* KCTC14780BP Polypeptide (0.0001%) | 31.3 |

As shown in the results of Table 13, it was confirmed that the NO production inhibitory ability was increased when the normal cells were treated with the *Saccharomyces cerevisiae* KCTC14780BP fermented product and the fraction containing the yeast polypeptide. In particular, the increase rate of *Saccharomyces cerevisiae* KCTC14780BP fermented product was superior compared to that of the normal yeast fermented product prepared under the same conditions.

Example 6-2. Confirmation of Skin Soothing and Inflammation Improvement Effects (Inhibition of NO Production) of *Lactobacillus* (*Lactobacillus fructivorans* KCTC14776BP) Fermented Product The confirmation of skin soothing and inflammation improvement effects was performed in the same manner as in Example 6-1 (Table 14).

TABLE 14

| Sample | NO Production Inhibitory Ability (% of control) |
| --- | --- |
| Normal cells (Negative control) | 0 |
| Normal cells + L-NMMA (Positive control, 20 µg/mL) | 47.9 |
| *Lactobacillus fructivorans* KCTC14776BP fermented product (1%) | 15.1 |
| Normal *Lactobacillus* fermented product (1%) | 4.9 |

As shown in the results of Table 14, it was confirmed that the NO production inhibitory ability was increased when the normal cells were treated with the *Lactobacillus fructivorans* KCTC14776BP fermented product. In particular, the increase rate of *Lactobacillus fructivorans* KCTC14776BP fermented product was superior compared to that of the normal *Lactobacillus* fermented product prepared under the same conditions.

Accordingly, it was found that the *Saccharomyces cerevisiae* KCTC14780BP fermented product and the fraction containing the yeast polypeptide, and/or the *Lactobacillus fructivorans* KCTC14776BP fermented product of the present invention exhibited excellent effects in skin soothing and inflammation improvement, etc.

Example 7. Confirmation of Melanin Expression Inhibitory Effect of Yeast (*Saccharomyces cerevisiae* KCTC14780BP) Fermented Product and Fraction Containing Yeast Polypeptide Samples were diluted in B16f10 melanocytes at each concentration, treated for 72 hours, and cultured, and then, the amount of melanin pigment present in melanocytes was quantified. The melanin production inhibitory rate was calculated in comparison to the total protein amount, and the values thereof were measured as percentage (%) based on the DMSO control (DMEM containing 0% serum) set to 100%.

In order to measure the degree of decrease in the amount of melanin pigment in the *Saccharomyces cerevisiae* KCTC14780BP fermented product and the fraction containing the yeast polypeptide, the inhibition rate of melanin production was compared upon treatment with the positive control group (Arbutin 200 ppm (Lim Y. J. et al., 2009, *Arch Pharm Res.*)), the *Saccharomyces cerevisiae* KCTC14780BP fermented product and the fraction containing the yeast polypeptide (Table 15).

TABLE 15

| Sample | Treatment Concentration (%) | Melanin Production Inhibition (%) |
|---|---|---|
| Positive control (Arbutin) | 0.02 | 56.4 |
| *Saccharomyces cerevisiae* KCTC14780BP fermented product | 0.01 | 34.6 |
| Fraction containing *Saccharomyces cerevisiae* KCTC14780BP polypeptide | 0.01 | 33.7 |
| | 0.001 | 33 |

As shown in the results of Table 15, it was confirmed that the melanin production inhibition rate was increased when the normal cells were treated with the *Saccharomyces cerevisiae* KCTC14780BP fermented product and the fraction containing the yeast polypeptide.

Accordingly, it was found that the *Saccharomyces cerevisiae* KCTC14780BP fermented product and the fraction containing the yeast polypeptide of the present invention exhibited excellent effect in skin whitening, etc.

Example 8. Confirmation of Free Radical Scavenging Effect of Yeast (*Saccharomyces cerevisiae* KCTC14780BP) Fermented Product and Fraction Containing Yeast Polypeptide After dissolving samples in DMSO, the equal amounts (100 μL) of 0.15 mM DPPH solution and the samples were mixed and reacted at room temperature for 30 minutes. Then, the color change of DPPH was measured by absorbance (A540) at 540 nm.

In order to evaluate the radical scavenging ability of the *Saccharomyces cerevisiae* KCTC14780BP fermented product and the fraction containing the yeast polypeptide, the radical scavenging ability was compared by measuring A540 values upon treatment with the positive control (Vitamin C), the *Saccharomyces cerevisiae* KCTC14780BP fermented product and the fraction containing the yeast polypeptide and obtaining $IC_{50}$ value (Table 16).

TABLE 16

| Sample | IC 50 (%) |
|---|---|
| Positive control (Vitamin C) | 0.000606 ± 0.00006 |
| *Saccharomyces cerevisiae* KCTC14780BP fermented product | 3.476 ± 0.337 |
| Fraction containing *Saccharomyces cerevisiae* KCTC14780BP polypeptide | 0.1804 ± 0.0174 |

As shown in the results of Table 16, the free radical (reactive oxygen species) scavenging effect was confirmed when the normal cells were treated with the *Saccharomyces cerevisiae* KCTC14780BP fermented product and the fraction containing the yeast polypeptide.

Accordingly, it was found that the *Saccharomyces cerevisiae* KCTC14780BP fermented product of the present invention exhibited excellent effects of antioxidation, antiaging and skin protection from external stimuli.

Example 9. Confirmation of Effect of Soothing Sensitive Skin of Fraction Containing Yeast Polypeptide of Yeast (*Saccharomyces cerevisiae* KCTC14780BP)

Example 9-1. Confirmation of Inhibitory Effect of Erythema/Itch-Inducing Factor Expression of Fraction Containing Yeast Polypeptide Samples treated with UVB (11 mJ) by diluting Raw 264.7 cells for each concentration were cultured for 24 hours. The prostaglandin E2 (PGE2) production inhibitory ability (%) was evaluated using a PGE2 quantitative kit. Specifically, a standard curve was prepared using 4PL regression, and the amount of PGE2 produced during sample treatment was calculated relative to the UVB-induced PGE2 production effect set as 100%, and the values were measured (Table 17).

TABLE 17

| Sample | Treatment Concentration (%) | PGE2 Production (%) |
|---|---|---|
| Control (UVB) | 11 mJ | 100 |
| Fraction containing *Saccharomyces cerevisiae* KCTC14780BP polypeptide | 0.1 | 67.5 |
| | 0.001 | 87.6 |

As shown in the results of Table 17, the inhibitory effect of PGE2 expression was confirmed when the normal cells were treated with the fraction containing the *Saccharomyces cerevisiae* KCTC14780BP polypeptide.

Accordingly, it was found that the fraction containing the yeast polypeptide of the present invention exhibited excellent effects such as relieving skin erythema/itching and soothing and improving sensitive skin, etc.

Example 9-2. Confirmation of Effect of Increasing Loricrin (LOR), a Major Component for Strengthening Skin Barrier, Expression of Fraction Containing Yeast Polypeptide After treating HaCaT cells with TNF-a (10 pg/mL) for 3 hours, samples were diluted for each concentration, mixed with TNF-a-treated HaCaT cells, and cultured for 24 hours. The degree of increase in the expression of loricrin (LOR), a major component of the skin barrier, was quantified using qPCR (Table 18).

TABLE 18

| Sample | Treatment Concentration (%) | LOR Gene Expression (Relative mRNA level, of control) |
|---|---|---|
| Untreated group | — | 1 |
| Control (TNF-a) | 10 pg/mL | 0.39 |
| Fraction containing *Saccharomyces cerevisiae* KCTC14780BP polypeptide | 0.1 | 0.52 |

As shown in the results of Table 18, it was confirmed that LOR expression was increased when the normal cells were treated with the fraction containing the *Saccharomyces cerevisiae* KCTC14780BP polypeptide.

Accordingly, it was found that the fraction containing the yeast polypeptide of the present invention exhibited excellent effects such as strengthening the skin barrier and soothing and improving sensitive skin, etc.

Example 9-3. Confirmation of Inflammatory Cytokine Inhibitory Effect of Fraction Containing Yeast Polypeptide Samples treated with UVB (11 mJ) by diluting HaCaT cells for each concentration were cultured for 24 hours. The expression level of the inflammatory cytokine (TNF-a) expressed in sensitive skin was calculated using qPCR and the value was measured (Table 19).

TABLE 19

| Sample | Treatment Concentration (%) | TNFa Gene Expression (Relative mRNA level, of control) |
|---|---|---|
| Untreated group | — | 1 |
| Control (UVB) | 11 mJ | 3.25 |
| Fraction containing *Saccharomyces cerevisiae* KCTC14780BP polypeptide | 0.1 | 2.09 |
| | 0.01 | 2.05 |

As shown in the results of Table 19, it was confirmed that the TNF-α expression was suppressed when the normal cells were treated with the fraction containing the *Saccharomyces cerevisiae* KCTC14780BP polypeptide.

Accordingly, it was found that the fraction containing the yeast polypeptide of the present invention exhibited excellent effects such as soothing and improving sensitive skin, etc.

Example 9-4. Confirmation of Inhibitory Effect of TRPV1 Activity, a Skin Nerve-Stimulating Inducer, of Fraction Containing Yeast Polypeptide HEK 293T-TRPV1 cells were treated with samples diluted for each concentration, and after 10 minutes, the inhibitory effect of TRPV1 (transient receptor potential vanilloid-1) activity was evaluated using a calcium influx detection assay kit (Table 20).

TABLE 20

| Sample | Treatment Concentration (%) | TRPV1 Activity (RFU, relative fluorescent unit) |
|---|---|---|
| Untreated group | — | 83.57 |
| Negative control (Capsaicin)*TRPV1 activity induction | 10 μM | 101.86 |
| Positive control (Capsazepin)*TRPV1 activity inhibition | 3 μM | 75.91 |
| Fraction containing *Saccharomyces cerevisiae* KCTC14780BP polypeptide | 0.1 | 75.68 |
| | 0.01 | 75.83 |

As shown in the results of Table 20, it was confirmed that the TRPV1 activity was inhibited when the normal cells were treated with the fraction containing the *Saccharomyces cerevisiae* KCTC14780BP polypeptide. In particular, it was confirmed that the TRPV1 activity inhibitory effect was superior than that of the positive control group treated under the same conditions.

Accordingly, it was found that the fraction containing the yeast polypeptide of the present invention exhibited excellent effects such as reduction of skin nerve irritation/pain, soothing and improvement of sensitive skin, etc.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method for improving skin, comprising:

applying a composition including any one or more of a strain selected from the group consisting of *Saccharomyces cerevisiae* deposited under Accession No. KCTC14779BP, *Saccharomyces cerevisiae* deposited under Accession No. KCTC14780BP, *Lactobacillus fructivorans* deposited under Accession No. KCTC14776BP, *Bacillus paramycoides* deposited under Accession No. KCTC14777BP, and *Bacillus megaterium* deposited under Accession No. KCTC14778BP, a culture of the strain, a fermented product of the strain, and a fraction of the culture or fermented product to a subject, wherein the composition is derived by centrifugation of a culture of the strain and sonication, wherein the skin improvement is any one or more selected from the group consisting of wrinkle improvement, elasticity improvement, prevention of aging, skin moisturization, skin soothing, skin regeneration, improvement of skin inflammation, skin whitening, antioxidation, anti-aging, soothing of sensitive skin, improvement of sensitive skin, alleviation of erythema, alleviation of itchiness, and enhancement of skin barrier function.

2. The method of claim 1, wherein the composition is a cosmetic or quasi-drug composition.

3. The method of claim 1, wherein the composition has the effects of promoting collagen synthesis, promoting hyaluronic acid synthesis, increasing cell activity, inhibiting NO production, inhibiting melanin expression, scavenging free radicals, inhibiting prostaglandin E2 (PGE2) expression, increasing loricrin (LOR) expression, inhibiting TNF-α expression, or inhibiting TRPV1 activity.

4. The method of claim 1, wherein the composition is for improving wrinkles and elasticity, anti-aging, or skin moisturization, and further wherein the strain comprises the *Saccharomyces cerevisiae* strain deposited under Accession No. KCTC14779BP.

5. The method of claim 1, wherein the composition is for skin soothing, skin regeneration, improvement of skin inflammation, skin moisturization, wrinkle improvement, elasticity improvement, skin whitening, antioxidation, anti-aging, soothing of sensitive skin, improvement of sensitive skin, alleviation of erythema, alleviation of itchiness, or enhancement of skin barrier function, and further wherein the strain comprises the *Saccharomyces cerevisiae* strain deposited under Accession No. KCTC14780BP.

6. The method of claim 1, wherein the composition is for improving wrinkles and elasticity, anti-aging, skin soothing, improving skin inflammation or skin moisturization, and further wherein the strain comprises the *Lactobacillus fructivorans* deposited under Accession No. KCTC14776BP.

7. The method of claim 1, wherein the composition is for improving wrinkles and elasticity, anti-aging, or skin moisturization, and further wherein the strain comprises the *Bacillus paramycoides* strain deposited under Accession No. KCTC14777BP.

8. The method of claim 1, wherein the composition is for skin moisturization, and further wherein the strain comprises the *Bacillus megaterium* strain deposited under Accession No. KCTC14778BP.

9. The method of claim 1, wherein the skin improvement comprises one or more of anti-aging, skin whitening, antioxidation, or prevention of aging.

* * * * *